United States Patent
Kaji et al.

(10) Patent No.: US 8,975,209 B2
(45) Date of Patent: Mar. 10, 2015

(54) SOLID SUPPORT-POLYMETHYLALUMINOXANE COMPLEX, METHOD FOR PRODUCING SAME, OLEFIN POLYMERIZATION CATALYST, AND METHOD FOR PRODUCING POLYOLEFIN

(75) Inventors: Eiichi Kaji, Yamaguchi (JP); Etsuo Yoshioka, Yamaguchi (JP)

(73) Assignee: Tosoh Finechem Corporation, Yamaguchi (JP)

( * ) Notice: Subject to any disclaimer, the term of this patent is extended or adjusted under 35 U.S.C. 154(b) by 0 days.

(21) Appl. No.: 13/697,012

(22) PCT Filed: May 11, 2011

(86) PCT No.: PCT/JP2011/060889
§ 371 (c)(1), (2), (4) Date: Nov. 9, 2012

(87) PCT Pub. No.: WO2011/142400
PCT Pub. Date: Nov. 17, 2011

(65) Prior Publication Data
US 2013/0059990 A1 Mar. 7, 2013

(30) Foreign Application Priority Data
May 11, 2010 (JP) ................................. 2010-109541

(51) Int. Cl.
*C08F 4/02* (2006.01)
*C08F 4/642* (2006.01)
*C08F 4/6592* (2006.01)
*C08F 10/02* (2006.01)
*C07F 5/06* (2006.01)
*C08F 4/659* (2006.01)
*C08F 110/02* (2006.01)

(52) U.S. Cl.
CPC ............... *C07F 5/066* (2013.01); *C07F 5/068* (2013.01); *C07B 2200/11* (2013.01); *C08F 4/65916* (2013.01); *C08F 4/65925* (2013.01); *C08F 110/02* (2013.01); *Y10S 526/943* (2013.01)
USPC ........... 502/439; 502/114; 502/120; 502/132; 502/152; 526/128; 526/129; 526/165; 526/348; 526/943

(58) Field of Classification Search
CPC ........ C08F 4/02; C08F 4/642; C08F 4/65912; C08F 4/65916; C08F 4/6592; C08F 10/02
USPC .......... 502/439, 120, 132, 152, 114; 526/128, 526/129, 160, 165, 943
See application file for complete search history.

(56) References Cited

U.S. PATENT DOCUMENTS

| 5,777,143 | A | 7/1998 | Malpass et al. |
| 5,831,109 | A | 11/1998 | Smith et al. |
| 6,034,024 | A | 3/2000 | Krzystowczyk et al. |
| 8,404,880 | B2 * | 3/2013 | Kaji et al. ..................... 556/179 |
| 2007/0197745 | A1 | 8/2007 | Kaji et al. |

FOREIGN PATENT DOCUMENTS

| CN | 1164241 A | 11/1997 |
| CN | 1209080 A | 2/1999 |
| EP | 1728795 A1 | 12/2006 |
| EP | 2360191 A1 | 8/2011 |
| JP | 61-108610 | 5/1986 |
| JP | 63-066206 | 3/1988 |
| JP | 02-173104 | 7/1990 |
| JP | 3117257 | 6/1993 |
| JP | 2000-505785 | 5/2000 |
| JP | 2001-502714 | 2/2001 |
| JP | 2005-263749 | 9/2005 |
| WO | WO2010/055652 | * 5/2010 |

OTHER PUBLICATIONS

International Search Report for corresponding International Application No. PCT/JP2011/060889, Jun. 14, 2011.
International Preliminary Report on Patentability for corresponding International Application No. PCT/JP2011/060889, Dec. 20, 2012.
Office Action for corresponding Chinese Application No, 201180023311.4, dated Aug. 19, 2014, 17 pages.
Extended European Search Report for corresponding European Application No. 11780657.0, 7, search completed Jun. 4, 2014, 7 pages.
Imhoff et al., "Characterization of Methylaluminoxanes and Determination of Trimethylaluminum Using Proton NMR", vol. 17, No. 10, 1998, pp. 1941-1945.
Office Action for corresponding Japanese Application No. 2012-514825, dated Jan. 6, 2015, 7 pages.

* cited by examiner

*Primary Examiner* — Caixia Lu
(74) *Attorney, Agent, or Firm* — Ditthavong & Steiner, P.C.

(57) ABSTRACT

Disclosed is a solid support-polymethylaluminoxane complex exhibiting a higher polymerization activity than a conventional substance and being homogeneous. Also disclosed is a method for producing an olefin-based polymer having a favorable quality using the complex and a transition metal compound. The complex comprises a coating layer containing polymethylaluminoxane and trimethylaluminum on the surface of a solid support. The coating layer comprises a solid polymethylaluminoxane composition in which (i) the content of aluminum is in a range of 36 to 41 mass % and (ii) the molar fraction of methyl groups derived from a trimethylaluminum moiety to the total number of moles of methyl groups is 12 mol % or less. Also disclosed is an olefin polymerization catalyst comprising the complex and a transition metal compound represented by general formula (III): $MR^5R^6R^7R^8$ as catalyst components, and a method for producing a polyolefin comprising polymerizing an olefin using the catalyst.

7 Claims, 4 Drawing Sheets

SOLID SUPPORT-POLYMETHYLALUMINOXANE COMPLEX, METHOD FOR PRODUCING SAME, OLEFIN POLYMERIZATION CATALYST, AND METHOD FOR PRODUCING POLYOLEFIN

CROSS-REFERENCE TO RELATED APPLICATIONS

This application claims benefit of priority to Japanese Patent Application No. 2010-109541 filed on May 11, 2010, which is expressly incorporated herein by reference in its entirety.

The present invention relates to a solid support-polymethylaluminoxane complex for use in polymerizing olefins, a method for producing the same, a polymerization catalyst employing a solid support-polymethylaluminoxane complex as a catalytic component, and a method for producing polyolefins.

BACKGROUND ART

Solution polyaluminoxane compositions are condensation products generally prepared by the partial hydrolysis of an organic aluminum compound. They are known to be useful as co-catalysts that efficiently activate the transition metal compounds serving as primary catalysts in the producing of olefin polymers. Polymethylaluminoxane compositions in which trimethylaluminum is employed as a starting material organic aluminum compound are widely known to perform particularly well as co-catalysts. These compositions are normally handled in the form of solutions obtained by dissolution in aromatic hydrocarbon solvents such as toluene.

Polymethylaluminoxane compositions perform well as co-catalysts. However, they are normally handled in a state where a primary catalyst such as a metallocene compound and polymethylaluminoxane composition have been dissolved in a solvent. Thus, the morphology of the polymer that is produced cannot be controlled. Not only does handling of the polymer present problems, but there is also a drawback in that fouling due to adhesion of the polymer to the polymerization reactor or the like occurs quite readily. Accordingly, use as is in slurry polymerization or vapor phase polymerization is problematic.

To solve these problems, a method of applying a supported solid polymethylaluminoxane composition—consisting of a polymethylaluminoxane composition supported on a solid inorganic support such as silica, alumina, or magnesium chloride—to suspension polymerization or vapor phase polymerization has been proposed. Silica is the most widely employed support among solid inorganic supports, and there are a number of examples of its use at the industrial level (see Patent References 1 to 5 and the like).

The above solid inorganic supports, including silica, are known to compromise the performance of polymers by tending to remain on the polymer, causing fisheyes, and the like. Solid polymethylaluminoxane compositions in which such supports have been employed are known to exhibit a greater drop in activity than in the polymerization activity in homogeneous system polymerization. Accordingly, to solve these problems, to reduce the negative impact of the support on the polymer while retaining the merits of a promoter in the form of a polymethylaluminoxane composition in a solid state, there is a need to develop a highly active supported solid polymethylaluminoxane composition.

Further, in methods known thus far, the compounds that can be employed as solid supports are limited. Not just any solid substance can be employed as a support. Even silica, which is industrially employed, must be controlled to achieve a pore size, pore capacity, and quantity of surface hydroxyl groups suited to the objective.

CITATION LIST

Patent References

Patent Reference 1: JP H02-173104 (1990)
Patent Reference 2: JP S63-66206 (1988)
Patent Reference 3: JP S61-108610 (1986)
Patent Reference 4: JP Patent 3117257
Patent Reference 5: JP 2000-505785
The entire contents of Patent References 1 to 5 are incorporated herein particularly by reference.

SUMMARY OF THE INVENTION

Problem to be Solved by the Invention

Among the methods known thus far, supported solid polymethylaluminoxane compositions that are prepared using a solid support such as silica generally present a problem in the form of polymerization activity that is much lower than that of liquid polymethylaluminoxane compositions. There is also a problem in that compounds that can be employed as solid supports are limited.

Accordingly, the problem to be solved by the present invention is to provide a solid support-polymethylaluminoxane complex, in which a solid support such as silica is employed, that affords greater polymerization activity than those obtained based on conventional formulas. The method of the present invention provides a homogeneous solid support-polymethylaluminoxane complex, even when using solid supports that have previously been difficult to employ.

In addition, another problem to be solved by the present invention is also to provide a method for inexpensively producing with good industrial efficiency a high-quality olefin polymer employing the above solid support-polymethylaluminoxane complex and a transition metal compound.

Means of Solving the Problems

The present invention, which solves the above-stated problems, is as follows.

[1]
A solid support-polymethylaluminoxane complex in which a coating layer containing polymethylaluminoxane and trimethylaluminum is present on at least part, or all, of the surface of a solid support.

[2]
The solid support-polymethylaluminoxane complex according to [1], wherein the coating layer contains trimethylaluminum and polymethylaluminoxane containing the unit denoted by general formula (I) below —[(Me)AlO]$_n$—     (I)

in the formula, n denotes an integer of from 10 to 50 and
   comprises a solid polymethylaluminoxane composition:
(i) in which the aluminum content falls within a range of from 36 mass % to 41 mass %, and
(ii) the mole fraction of methyl groups contributed from trimethylaluminum moieties relative to the total number of moles of methyl groups is equal to or less than 12 mol %.

[3]
The solid support-polymethylaluminoxane complex according to [1] or [2], wherein the complex has a specific surface area falls within a range of 10 to 100 m²/mmol-Al.

[4]
The solid support-polymethylaluminoxane complex according to any one of [1] to [3], wherein the solid support is silica, alumina, magnesium chloride, magnesium oxide, titania, zirconia, activated carbon, zeolite, carbon nanotubes, polystyrene beads, or complexes thereof.

[5]
The solid support-polymethylaluminoxane complex according to any one of [1] to [4], wherein the mass ratio (support: coating layer) of the solid support to the coating layer containing polymethylaluminoxane and trimethylaluminum falls within a range of from 1:0.1 to 1:100.

[6]
A method for producing a solid support-polymethylaluminoxane complex comprising forming on a solid support surface a coating layer containing polymethylaluminoxane and trimethylaluminum by heating the solid support and an aromatic hydrocarbon solution containing trimethylaluminum and polymethylaluminoxane containing the unit denoted by general formula (I) below, hereinafter referred to as a solution polymethylaluminoxane composition:

$$—[(Me)AlO]_n— \quad (I)$$

in the formula, n denotes an integer of from 1 to 50;
wherein the mole fraction of methyl groups contributed from trimethylaluminum moieties relative to the total number of moles of methyl groups is equal to or less than 20 mol % in the solution polymethylaluminoxane composition.

[7]
The producing method according to [6], wherein in the heat treatment of the solution polymethylaluminoxane composition and the solid support, a heating temperature and heating period suited to the formation of the coating layer are selected from:
(i) the heating temperature falling within a range of 80 to 200° C., and
(ii) the heating period being equal to or more than 5 minutes but less than 24 hours.

[8]
The producing method according to [6] or [7], wherein the solution polymethylaluminoxane composition is obtained by thermally decomposing an alkyl aluminum compound comprising aluminum-oxygen-carbon bonds.

[9]
The producing method according to [8], wherein the alkyl aluminum compound containing aluminum-oxygen-carbon bonds is prepared by reacting trimethylaluminum with an oxygen-containing organic compound.

[10]
The producing method according to [9], wherein the oxygen-containing organic compound is an aliphatic or aromatic carboxylic acid denoted by general formula (II) below:

$$R^1—(COOH)_n \quad (II)$$

in the formula, $R^1$ denotes a hydrocarbon group in the form of a C1 to C20 linear or branched alkyl group, alkenyl group, or aryl group and n denotes an integer of from 1 to 5.

[11]
The producing method according to [9] or [10], wherein the reaction of the trimethylaluminum and oxygen-containing organic compound is conducted such that the molar ratio of aluminum atoms contained in the trimethylaluminum to the oxygen atoms contained in the oxygen-containing compound (Al/O) falls within a range of from 1.15 to 1.4:1.

[12]
The producing method according to any one of [6] to [11], wherein the solid support is silica, alumina, magnesium chloride, magnesium oxide, titania, zirconia, activated carbon, zeolite, carbon nanotubes, polystyrene beads, or complexes thereof.

[13]
An olefin polymerization catalyst comprising the solid support-polymethylaluminoxane complex according to any one of [1] to [5] and a transition metal compound denoted by general formula (III) below as catalyst components:

$$MR^5R^6R^7R^8 \quad (III)$$

in the formula, M denotes a transition metal element, and $R^5$, $R^6$, $R^7$, and $R^8$ denote an organic group having a cycloalkadienyl skeleton jointly, alkyl group, alkoxy group, aryloxy group, alkylsilyl group, alkylamide group, alkylimide group, alkylamine group, alkylimine group, or halogen atom.

[14]
A method for producing polyolefins, comprising using the catalyst according to [13] to polymerize an olefin.

Effect of the Invention

According to the present invention, it is possible to extremely conveniently obtain at high yield solid support-polymethylaluminoxane complexes using solid supports that have conventionally been difficult to employ. High polymerization activity is exhibited when the solid support-polymethylaluminoxane complexes of the present invention are employed as co-catalysts.

MODES OF CARRYING OUT THE INVENTION

Solid Support-Polymethylaluminoxane Complex

The solid support-polymethylaluminoxane complex of the present invention is a complex having a coating layer containing polymethylaluminoxane and trimethylaluminum on at least part, or all, of the surface of a solid support.

The solid support-polymethylaluminoxane complex of the present invention has a coating layer containing polymethylaluminoxane and trimethylaluminum. The state in which the polymethylaluminoxane and trimethylaluminum are present in the coating layer is unclear.

By way of example, the coating layer is desirably comprised of a solid polymethylaluminoxane composition:
(i) in which the aluminum content falls within a range of from 36 mass % to 41 mass %, and
(ii) the mole fraction of methyl groups contributed from trimethylaluminum moieties relative to the total number of moles of methyl groups is equal to or less than 12 mol %.

By way of example, the polymethylaluminoxane can be one containing the unit denoted by general formula (I) below $$-[(Me)AlO]_n- \qquad (I)$$

In the formula, n denotes an integer of from 10 to 50).

The phrase "containing the unit denoted by general formula (I) below" means that it contains polymethylaluminoxane in which n is a single number (n denotes a specific integer) falling within the above range or multiple polymethylaluminoxanes in which n is of multiple types (n denotes multiple different integers). n being an integer of from 10 to 50 is based on that the n of the polymethylaluminoxane in the solution polymethylaluminoxane composition serving as the starting material of the coating liquid of the solid support-polymethylaluminoxane complex being from 10 to 50. In the literature, it is reported that in some cases, disproportionation of the polymethylaluminoxane chains in the solution polymethylaluminoxane composition, or of the polymethylaluminoxane chains and the trimethylaluminum, changes the length of the polymethylaluminoxane chains. When a disproportionation reaction occurs between polymethylaluminoxane chains, trimethylaluminum is produced. When a disproportionation reaction occurs between a polymethylaluminoxane chain and trimethylaluminum, trimethylaluminum is consumed. In the present invention, "polymethylaluminoxane" can be of a chain structure, cyclic structure, or branched structure so long as the above unit is contained.

When the polymethylaluminoxane is of a cyclic structure, the theoretical quantity of aluminum is 46.5 mass %, and the theoretical quantity of aluminum in the trimethylaluminum is 37.4 mass %. That is, in cases where the content of aluminum in the coating layer of the solid support-polymethylaluminoxane complex exceeds 46 mass %, the coating layer is presumed to be comprised of polymethylaluminoxane having a nearly cyclic structure, with almost no trimethylaluminum present and with no impurities such as solvents being contained. When the polymethylaluminoxane assumes a linear structure, the theoretical content of aluminum changes with the number n in general formula (I), but is smaller than in the cyclic structure. Additionally, since polymethylaluminoxane of linear and branched structures is contained in the coating layer of the solid support-polymethylaluminoxane complex of the present invention in addition to polymethylaluminoxane of cyclic structure, and since impurities such as residual solvent are contained in addition to trimethylaluminum, in the coating layer of the solid support-polymethylaluminoxane complex of the present invention, it is suitable for the aluminum content to fall within a range of from 36 mass % to 41 mass %, as indicated by (i). The lower the aluminum content, the greater the proportion of trimethylaluminum present. The higher the aluminum content, the smaller the proportion of trimethylaluminum present tends to be.

Keeping the aluminum content to within a range of from 36 mass % to 41 mass % is desirable to impart homogeneity and strength to the coating layer of the solid support-polymethylaluminoxane complex so that fracturing does not occur due to crack and the like. Conversely, an aluminum content of less than 36 mass % indicates that excessive impurities such as solvent are contained due to insufficient drying. When the aluminum content exceeds 46 mass %, polymethylaluminoxane of primarily cyclic structure is presumed to constitute the coating layer, with almost no trimethylaluminum and solvent impurities being contained. However, the solid polymethylaluminoxane composition that is obtained according to the present invention will be different in composition. From the above perspective, the aluminum content desirably falls within a range of from 38 mass % to 41 mass %.

The aluminum content of the solid support-polymethylaluminoxane complex and solution polymethylaluminoxane composition prepared in the present invention can be determined, for example, by adding an excess quantity of disodium ethylenediaminetetraacetate to a solution obtained by hydrolysis with 0.5N sulfuric acid aqueous solution, employing dithizone as an indicator, and performing a back titration with zinc sulfate. When the concentration being measured is weak, measurement can be conducted by atomic absorption spectrometry.

The mass of the polymethylaluminoxane composition in the coating layer is often determined as the difference between the mass of the solid support-polymethylaluminoxane complex and the mass of the material remaining after removing the coating layer by hydrolysis. When the support is soluble in acid, it is also possible to use composition analysis values. When the solid support is porous, the composition can be analyzed after an acid-insoluble solid support is dissolved.

The total number of moles of methyl groups in the mole fraction of methyl groups contributed from trimethylaluminum moieties relative to the total number of moles of methyl groups indicated in (ii) is the total number of moles of methyl groups contributed from trimethylaluminum and methyl groups contributed from polymethylaluminoxane. The number of moles of methyl groups contributed from trimethylaluminum moieties is the number of moles of methyl groups contributed from trimethylaluminum. The mole fraction of methyl groups contributed from trimethylaluminum moieties is equal to or less than 12 mol %. The fact that the low mole fraction of methyl groups contributed from trimethylaluminum moieties means that there are few methyl groups contributed from trimethylaluminum moieties contained in the polymethylaluminoxane composition, and that there is much aluminum in polymethylaluminoxane chains. Keeping the mole fraction of methyl groups contributed from trimethylaluminum moieties to equal to or less than 12 mol % yields a strong solid support-polymethylaluminoxane complex of low solvent solubility in which the particles are not destroyed by the drying treatment. Conversely, when the mole fraction of methyl groups contributed from trimethylaluminum moieties exceeds 12 mol %, solubility in solvent increases and the particles exhibit a tendency to crush readily.

The mole fraction of methyl groups contributed from trimethylaluminum moieties in the solid support-polymethylaluminoxane complex of the present invention is desirably equal to or less than 11 mol %. For example, the lower limit of the mole fraction of methyl groups contributed from trimethylaluminum moieties can be 6 mol %, desirably 8 mol %, because it depends on the solution polymethylaluminoxane serving as a starting material, controlling the shape of the solid support-polymethylaluminoxane complex.

The solution polymethylaluminoxane composition employed in the present invention contains trimethylaluminum that is present in the unreacted starting materials. In the present invention, the quantity of trimethylaluminum that is present in the polymethylaluminoxane composition is expressed as the mole fraction of methyl groups contributed from trimethylaluminum relative to the total number of moles of methyl groups contributed from trimethylaluminum and polymethylaluminoxane (abbreviated as Me(TMAL)). Similarly, the quantity of polymethylaluminoxane present in the polymethylaluminoxane composition is expressed as the mole fraction of methyl groups contributed from polymethylaluminoxane relative to the total number of moles of methyl groups contributed from trimethylaluminum and polymethylaluminoxane (abbreviated as Me(PMAO)).

The mole fractions of the components of the solution polymethylaluminoxane composition and solid support-polymethylaluminoxane complex can be determined from the surface area ratios assigned to the various components in $^1$H-NMR measurement of the polymethylaluminoxane composition. Methods of obtaining the specific Me(PMAO) and Me (TMAL) mole fractions of polymethylaluminoxane compositions are exemplified in the Examples.

The volume-based median diameter and particle size distribution of the solid support-polymethylaluminoxane complex of the present invention can be obtained by the laser diffraction and scattering method in a dry nitrogen atmosphere using a Master Sizer 2000 Hydro S from Malvern Instrument Ltd. The specific method is described in the Examples.

The solid support-polymethylaluminoxane complex of the present invention is particulate with a specific surface area that desirably falls within a range of 10 to 100 m$^2$/mmol-Al. Since the specific surface area of the particulate solid support-polymethylaluminoxane complex of the present invention falls within the above range, it is possible to achieve good activity in the polymerization of olefin compounds using the solid support-polymethylaluminoxane complex and a transition metal compound. Here, the term "good activity" desirably means greater activity than that of a solid support-methylaluminoxane composition obtained by the usual methods using silica as the solid support. However, the good polymerization activity of the solid support-polymethylaluminoxane complex of the present invention does not just depend on the specific surface area. Cases where it depends on components and structures other than the specific surface area of the solid support-polymethylaluminoxane complex are also conceivable. The specific surface area is thought to affect activation due to contact with transition metal compounds such as metallocene compounds serving as primary catalysts and solid support-polymethylaluminoxane complexes when employed in the polymerization of olefin compounds. That is, in general, the lower the specific surface area, the lower the activation efficiency of the primary catalyst, and the higher the specific surface area, the better the activation efficiency is thought to be. However, when the specific surface area is excessively high, the interior of the solid support-polymethylaluminoxane complex becomes too porous, and the strength of the solid is thought to decrease. For these reasons, the specific surface area desirably falls within a range of 10 to 100 m$^2$/mmol-Al, preferably within a range of 15 to 85 m$^2$/mmol-Al, and more preferably, within a range of 20 to 70 m$^2$/mmol-Al.

The specific surface area of the solid support-polymethylaluminoxane complex of the present invention can be determined using the BET adsorption isotherm equation and the phenomenon of vapor adsorption on solid surfaces. The specific method is described in the Examples.

The solid support is not specifically limited. So long as it is a solid substance that is substantially inert relative to polymethylaluminoxane based on the producing method of the present invention described further below, it is not limited. Examples of such solid substances are silica, alumina, magnesium chloride, magnesium oxide, titania, zirconia, activated carbon, zeolite, carbon nanotubes, polystyrene beads, and complexes thereof. However, there is no intent to limit the solid support thereto. Nor is the particle diameter of the solid support specifically limited. However, taking into account the ease of combination with a metallocene compound serving as the primary catalyst, the minimum particle diameter can fall within a range of 100 nm to 1,000 μm, desirably within a range of from 500 nm to 100 μm. However, there is no intent to limit the particle diameter thereto.

In the solid support-polymethylaluminoxane complex of the present invention, the mass ratio (support:coating layer) of the solid support to the coating layer containing polymethylaluminoxane and trimethylaluminum can be suitably determined taking into account the particle diameter of the solid support and the desired thickness of the coating layer. For example, it can fall within a range of from 1:0.1 to 1:100, desirably within a range of from 1:0.5 to 1:50. The thinner the coating layer the better due to the greater utilization rate of the aluminum contained in the coating layer. For example the thickness can fall within a range of 0.1 to 20 μm, desirably within a range of 0.2 to 10 μm. However, there is no intent to limit the thickness thereto.

[The Method for Producing a Solid Support-Polymethylaluminoxane Complex]

The method for producing a solid support-polymethylaluminoxane complex of the present invention comprises the step of forming on the surface of a solid support a coating layer containing polymethylaluminoxane and trimethylaluminum by heating a solid support and an aromatic hydrocarbon solution (solution polymethylaluminoxane composition) containing trimethylaluminum and polymethylaluminoxane containing the unit denoted by general formula (I) below:

—[(Me)AlO]$_n$—     (I)

In the formula, n denotes an integer of from 1 to 50.

The phrase "containing the unit denoted by general formula (I)" means containing polymethylaluminoxane in which n is a single number falling within the above range (n denotes a specific integer) or containing multiple polymethylaluminoxanes in which n denotes multiple numbers falling within the above range (n denotes multiple different integers). Defining n as an integer of from 10 to 50 causes the degree of polymerization of aluminoxane based on the molecular weight as determined by depression of the freezing point in benzene to fall within a range of 10 to 50.

The solution polymethylaluminoxane composition that is employed as a starting material in the producing method of the present invention can be prepared, for example, by the method described in Patent Reference 5. The method described in Patent Reference 5 is a method of preparing polymethylaluminoxane composition without hydrolysis of trimethylaluminum. Specifically, an alkyl aluminum compound having aluminum-oxygen-carbon bonds is thermally decomposed to obtain a solution polymethylaluminoxane composition.

Examples of aromatic hydrocarbons that can be employed in the solution polymethylaluminoxane composition are: benzene, toluene, ethylbenzene, propylbenzene, butylbenzene, xylene, chlorobenzene, and dichlorobenzene. There is no limitation to these examples; any aromatic hydrocarbon can be employed as the solvent for the solution polymethylaluminoxane composition.

The alkyl aluminum compound having aluminum-oxygen-carbon bonds is desirably prepared by reacting trimethylaluminum and an oxygen-containing organic compound. The oxygen-containing organic compound is desirably an aliphatic or aromatic carboxylic acid denoted by general formula (II):

$$R^1\text{—}(COOH)_n \tag{II}$$

In the formula, $R^1$ denotes a hydrocarbon group in the form of a C1 to C20 linear or branched alkyl group, alkenyl group, or aryl group and n denotes an integer of from 1 to 5.

The oxygen-containing compound that is employed in the reaction of an oxygen-containing compound and trimethylaluminum to obtain an alkyl aluminum compound having aluminum-oxygen-carbon bonds that yields a solution polymethylaluminoxane composition upon thermal decomposition is a carboxylic anhydride or carboxylic acid compound having a COOH group. When preparing the solution polymethylaluminoxane composition, one or more of these compounds can be employed. Specific examples of the oxygen-containing compound are formic acid, acetic acid, propionic acid, n-butyric acid, n-valeric acid, n-caproic acid, n-enanthic acid, n-caprylic acid, n-pelargonic acid, n-capric acid, n-lauric acid, n-myristic acid, n-stearic acid, oxalic acid, malonic acid, succinic acid, glutaric acid, adipic acid, pimelic acid, suberic acid, azelaic acid, sebacic acid, benzoic acid, phthalic acid, citric acid, tartaric acid, lactic acid, malic acid, toluic acid, toluic anhydride, acetic anhydride, propionic anhydride, n-butyric anhydride, n-valeric anhydride, n-caproic anhydride, oxalic anhydride, malonic anhydride, succinic anhydride, glutaric anhydride, benzoic anhydride, phthalic anhydride, and toluic anhydride. Of these, acetic acid, acetic anhydride, propionic acid, propionic anhydride, benzoic acid, benzoic anhydride, phthalic acid, phthalic anhydride, toluic acid, and toluic anhydride are desirable.

The molar ratio (Al/O) of the aluminum atoms contained in the trimethylaluminum and the oxygen atoms of the oxygen-containing organic compound employed in the synthesis of the solution polymethylaluminoxane composition can be set as desired to control the molecular weight of the polymethylaluminoxane or the residual quantity of trimethylaluminum. The ratio of the molar quantity of the aluminum atoms contained in the trimethylaluminum to the oxygen atoms of the oxygen-containing organic compound can be set anywhere within a range of 0.5 to 3.0:1. From the perspectives of ease of preparation of the solution polymethylaluminoxane composition, its stability, and suitably controlling the quantity of residual trimethylaluminum, the ratio of the molar quantities desirably falls within a range of 1.0 to 1.7:1, preferably within a range of 1.15-1.4:1.

The thermal decomposition of the aluminum compound containing aluminum-oxygen-carbon bonds that is a precursor of the solution polymethylaluminoxane composition can be conducted at any temperature from 20 to 90° C. From the perspectives of ease of handling the reaction, stability, and a suitably reaction time, 30 to 80° C. is desirable and 60 to 80° C. is preferred. The period of thermal decomposition of the aluminum compound having aluminum-oxygen-carbon bonds will vary with the thermal decomposition temperature and composition of the starting material (such as the Al/O molar ratio). By way of example, this period will fall within a range of 5 to 200 hours. The lower the temperature, the longer the period required. The higher the temperature, the shorter the period within which thermal decomposition can be completed.

When the thermal decomposition temperature exceeds 100° C., a gel product is generated in pronounced fashion, decreasing the recovery yield of uniform polymethylaluminoxane solution. Conversely, when the thermal decomposition temperature drops below 50° C., the increased period of the polymethylaluminoxane producing reaction sometimes causes a drop in productivity.

The concentration of the polymethylaluminoxane composition in the inert hydrocarbon solvent can fall within a range of 6 to 40 mass %, desirably 6 to 30 mass %, and preferably 10 to 25 mass %.

In nearly all the literature to-date on obtaining solution polymethylaluminoxane compositions by the thermal decomposition reaction of an aluminum compound having aluminum-oxygen-carbon bonds, it is emphasized that the solution polymethylaluminoxane composition is obtained at a quantitative reaction yield and that the quantity of trimethylaluminum in the solution polymethylaluminoxane composition can be controlled. Generally, trimethylaluminum does not have an effect as an activating agent on transition metal compounds, including metallocenes, so controlling the quantity of trimethylaluminum remaining in the solution polymethylaluminoxane composition is an important problem. However, when preparing a solution polymethylaluminoxane composition by hydrolysis, it is known that unless the concentration of aluminum in the reaction solution is lowered and the quantity of water added to the starting material trimethylaluminum is kept down, the aluminum recovery rate will drop precipitously.

A mole fraction of methyl groups contributed from trimethylaluminum moieties relative to the total number of moles of methyl groups of 20 mol % or lower in the solution polymethylaluminoxane composition that is employed as a starting material is desirable from the perspective of increasing the yield of aluminum recovered as a coating layer on the solid support-polymethylaluminoxane complex. The mole fraction of methyl groups contributed from trimethylaluminum moieties relative to the total number of methyl groups is desirably equal to or lower than 15 mol %. The lower limit of the mole fraction of methyl groups contributed from trimethylaluminum moieties relative to the total number of moles of methyl groups is about 6 mol %. Solution polymethylaluminoxane compositions prepared by hydrolysis have mole fractions denoted as the number of moles of methyl groups contributed from trimethylaluminum moieties relative to the total number of moles of methyl groups of 40 to 50 mol %, making it difficult to lower the mole fraction of methyl groups contributed from trimethylaluminum moieties relative to the total number of moles of methyl groups in the polymethylaluminoxane composition to below 15 mol % by normal concentration drying treatments. Conversely, in the preparation of solution polymethylaluminoxane compositions by thermal decomposition, by keeping the molar ratio of aluminum atoms contained in the trimethylaluminum to the oxygen atoms of the oxygen-containing organic compound to 1.15, it is possible to keep the mole fraction of methyl groups contributed from aluminoxane moieties relative to the total number of moles of methyl groups to 8 mol % while retaining good properties in the solid support-polymethylaluminoxane complex obtained. When a molar ratio of the aluminum atoms in the trimethylaluminum to the oxygen atoms in the oxygen-containing organic compound of 1.10 is employed, a molar ratio of methyl groups contributed from trimethylaluminum moieties relative to the total number of moles of methyl groups of 5.2 mol % can be achieved, but the properties of the solid support-polymethylaluminoxane complex will be poor. For these reasons, 8 to 14 mol % is desirable.

The aromatic hydrocarbon employed in the method of producing a solid support-polymethylaluminoxane complex of the present invention is not specifically limited. Examples are: benzene, toluene, ethylbenzene, propylbenzene, butylbenzene, xylene, chlorobenzene, and dichlorobenzene.

In the heat treatment, a heating temperature and heating period suited to the formation of the coating layer are desirably selected from:
(i) the heating temperature falling within a range of 80 to 200° C., and
(ii) the heating period being equal to or longer than 5 minutes but less than 24 hours.

The present inventors discovered that when a specific aromatic hydrocarbon solution containing trimethylaluminum and polymethylaluminoxane containing the unit denoted by general formula (I) (solution polymethylaluminoxane composition) was continuously heated to a prescribed temperature in the presence of a solid support, a coating layer of solid polymethylaluminoxane composition containing polymethylaluminoxane and trimethylaluminum formed on the solid support surface. The prescribed temperature ranges from 80 to 200° C. The time required for precipitation varies with the temperature. For example, it ranges from equal to or longer than 5 minutes to less than 24 hours. Remaining within this range makes it possible to obtain at high yield particles of solid support-polymethylaluminoxane complex regardless of the properties of the solid support. However, depending on the heating temperature, there are sometimes cases where heating is suitably conducted for a period exceeding this range. The precipitation of the coating layer of solid polymethylaluminoxane composition onto the surface of the solid support increases over time, reaching a nearly quantitative level. The composition of the solution polymethylaluminoxane composition and the concentration of the solute in the solvent (aromatic hydrocarbon solution) will also affect the amount of precipitate (recovery rate).

The heating temperature can be 80 to 200° C., is desirably 90 to 150° C., and is preferably 100 to 130° C. At this temperature range, the heating period is desirably 1 to 20 hours, preferably 5 to 12 hours. However, when the temperature is low, the time required for the solid polymethylaluminoxane composition to precipitate onto the surface of the solid support increases. When the temperature is high, the time required for precipitation tends to shorten.

The producing method of the present invention can further comprise a step of washing the solid support-polymethylaluminoxane complex obtained with a nonaromatic hydrocarbon solvent. Examples of the nonaromatic hydrocarbon solvent employed in washing are n-pentane, n-hexane, cyclohexane, methylcyclohexane, ethylcyclohexane, n-heptane, n-octane, n-decane, n-undecane, and Isopar E. Since the goal of the nonaromatic solvent employed in the present invention is to facilitate washing and drying of the solid support-polymethylaluminoxane complex obtained, low boiling solvents that facilitate drying of the solid polymethylaluminoxane, specifically, n-pentane, n-hexane, and cyclohexane, are desirable.

In the producing method, the solid support-polymethylaluminoxane complex of the present invention can be dispersed in a solvent as a dispersion, or can be a powder from which the solvent has been removed and that has been dried as needed. The powder can be dried, for example, by the method of removing the solvent under reduced pressure or a method employing a dry, heated nitrogen flow. When drying the solid support-polymethylaluminoxane complex of the present invention, in contrast to the case of the solution polymethylaluminoxane composition, the goal is just to remove the solvent adhering to the solid. Since there is no scattering of trimethylaluminum, there is no problem with employing a vacuum pump.

[Polymerization Catalyst for Olefins]

The present invention includes a polymerization catalyst for olefins. The polymerization catalyst for olefins of the present invention contains the solid support-polymethylaluminoxane complex of the present invention and a transition metal compound denoted by general formula (III) below as catalyst components:

$$MR^5R^6R^7R^8 \qquad (III)$$

(wherein M denotes a transition metal element, and $R^5$, $R^6$, $R^7$, and $R^8$ denote an organic group having a cycloalkadienyl skeleton jointly, alkyl group, alkoxy group, aryloxy group, alkylsilyl group, alkylamide group, alkylimide group, alkylamine group, alkylimine group, or halogen atom).

The solid support-polymethylaluminoxane complex of the present invention can be combined with catalysts known to be olefin polymerization catalysts and used as polymerization catalysts. Examples of olefin polymerization catalysts are transition metal compounds. Such transition metal compounds can be those denoted by general formula (III) above.

Specific examples of M in general formula (III) are: titanium, zirconium, hafnium, chromium, vanadium, manganese, iron, cobalt, nickel, and palladium. Titanium, zirconium, chromium, iron, and nickel are desirable.

Metallocene compounds in which 1 or 2 ligands having cycloalkadienyl skeletons are coordinated in general formula (III) are desirable as transition metal compounds. Examples of ligands having cycloalkadienyl skeletons are cyclopentadienyl groups, methylcyclopentadienyl groups, ethylcyclopentadienyl groups, butylcyclopentadienyl groups, dimethylcyclopentadienyl groups, pentamethylcyclopentadienyl groups, other alkyl-substituted cyclopentadienyl groups, indenyl groups, and fluorenyl groups. The cycloalkadienyl groups can be crosslinked with divalent substituted alkylene groups, substituted silylene groups, and the like.

Examples of ligands other than ligands having cycloalkadienyl skeletons are hydrocarbon groups with 1 to 20 carbon atoms, alkoxy groups, aryloxy groups, alkylsilyl groups, amine groups, imine groups, halogen atoms, and hydrogen atoms. Examples of hydrocarbons having 1 to 20 carbon atoms are alkyl groups, cycloalkyl groups, aryl groups, and aralkyl groups. Specific examples of alkyl groups are methyl groups, ethyl groups, propyl groups, isopropyl groups, and butyl groups. Specific examples of cycloalkyl groups are cyclopentyl groups and cyclohexyl groups. Specific examples of aryl groups are phenyl groups and tolyl groups. Specific examples of aralkyl groups are benzyl groups. Specific examples of alkoxy groups are methoxy groups, ethoxy groups, and butoxy groups. Specific examples of aryloxy groups are phenoxy groups. These groups can also be substituted with halogen atoms and the like. Specific examples of alkylsilyl groups are trimethylsilyl groups and triethylsilyl groups. Specific examples of halogens are fluorine, chlorine, bromine, and iodine.

Specific examples of transition metal compounds containing a ligand having a cycloalkanedienyl skeleton when M in general formula (III) is zirconium are: bis(cyclopentadienyl)zirconium monochloride monohydride, bis(cyclopentadienyl)zirconium monobromide monohydride, bis(cyclopentadienyl)methylzirconium hydride, bis(cyclopentadienyl)ethylzirconium hydride, bis(cyclopentadienyl)phenylzirconium hydride, bis(cyclopentadienyl)

benzylzirconium hydride, bis(cyclopentadienyl) neopentylzirconium hydride, bis(methylcyclopentadienyl) zirconium monochloride hydride, bis(indenyl)zirconium monochloride hydride, bis(cyclopentadienyl)zirconium dichloride, bis(cyclopentadienyl)zirconium dibromide, bis(cyclopentadienyl)methylzirconium monochloride, bis(cyclopentadienyl)ethylzirconium monochloride, bis(cyclopentadienyl)cyclohexylzirconium monochloride, bis(cyclopentadienyl)phenylzirconium monochloride, bis(cyclopentadienyl)benzylzirconium monochloride, bis(methylcyclopentadienyl)zirconium dichloride, bis(dimethylcyclopentadienyl)zirconium dichloride, bis(n-butylcyclopentadienyl)zirconium dichloride, bis(indenyl)zirconium dichloride, bis(indenyl)zirconium dibromide, bis(cyclopentadienyl)zirconium dimethyl, bis(cyclopentadienyl)zirconium diphenyl, bis(cyclopentadienyl)zirconium dibenzyl, bis(cyclopentadienyl)zirconium monomethoxymonochloride, bis(cyclopentadienyl)zirconium monoethoxymonochloride, bis(methylcyclopentadienyl)zirconium monoethoxymonochloride, bis(cyclopentadienyl)zirconium monophenoxymonochloride, and bis(fluorenyl)zirconium dichloride.

Specific examples of transition metal compounds in which M in general formula (III) denotes zirconium, that contain at least two ligands having cycloalkadienyl skeletons, and in which the at least two ligands having cycloalkadienyl skeletons are bonded through ethylenes, propylenes, other alkylene groups, isopropylidenes, diphenylmethylenes, other substituted alkylene groups, silylene groups, dimethylsilylenes, or other substituted silylene groups are: ethylene bis(indenyl)dimethylzirconium, ethylene bis(indenyl)diethylzirconium, ethylene bis(indenyl)diphenylzirconium, ethylene bis(indenyl)methylzirconium monochloride, ethylene bis(indenyl)ethylzirconium monochloride, ethylene bis(indenyl)methylzirconium monobromide, ethylene bis(indenyl)zirconium dichloride, ethylene bis(indenyl)zirconium bromide, and ethylene bis(4,5,6-tetrahydro-1-indenyl)zirconium dichloride. These can be in racemic form, meso form, or combinations thereof.

In homogeneous system polymerization, one of these transition metal compounds can be employed alone, or two or more can be employed to adjust the molecular weight distribution or the like. When a solid catalyst is prepared in advance, one of these transition metal compounds can be employed alone or two or more can be employed to adjust the molecular weight distribution or the like.

[Method for Producing Polyolefins]

The present invention includes a method for producing polyolefins comprising polymerizing an olefin with the catalyst of the present invention.

In homogeneous system polymerization employing the solid support-polymethylaluminoxane complex of the present invention and in polymerization employing a supported catalyst prepared with the solid support-polymethylaluminoxane complex of the present invention, suitable performance is achieved in methods where the form of polymerization is solution polymerization employing a solvent, bulk polymerization not employing a solvent, vapor phase polymerization, and the like. Good performance is also achieved in both continuous polymerization and batch polymerization methods. The use of hydrogen or the like as a molecular weight-regulating agent is also possible as needed.

The monomer employed in polymerization can be a single olefin monomer or compounds that can be employed in copolymerization combining such monomers. Specific examples are ethylene, propylene, 1-butene, 1-pentene, 1-hexene, 1-decene, 1-hexadecene, 1-octadecene, 1-eicosene, other α-olefins, bisfluoroethylene, trifluoroethylene, tetrafluoroethylene, hexafluoropropylene, other halogen-substituted olefins, cyclopentene, cyclohexene, norbornene, and other cyclic olefins.

EXAMPLES

The present invention is described in detail below through Examples. However, the present invention is not limited to the Examples.

In the Examples set forth below, the solid support-polymethylaluminoxane complex was normally dried at 40° C. through a sealed pot charged with fluid paraffin under a full vacuum generated with a vacuum pump. Drying was terminated at the point where no air bubbles were observed within the sealed pot.

Test Methods (1) Aluminum Content

The aluminum content of the solution polymethylaluminoxane composition and the solid support-polymethylaluminoxane complex was basically measured by adding an excess quantity of disodium ethylenediamine tetraacetate to a solution that had been hydrolyzed with a 0.5N sulfuric acid aqueous solution, employing dithizone as an indicator, and performing a back titration with zinc sulfate. When the concentration being measured was weak, measurement was conducted by atomic absorption spectrometry.

(2) The Specific Surface Area of the Solid Support-Polymethylaluminoxane Complex The specific surface area of the solid support-polymethylaluminoxane complex in the present invention was expressed as the surface area per quantity of Al (mmol-Al) contained in the solid support-polymethylaluminoxane complex. Specifically, the BET adsorption isotherm equation and the phenomenon of vapor adsorption on solid surfaces were utilized to determine the specific surface area ($m^2/g$), which was converted using the following equation. In the conversion equation, Y denotes the Al mass % in the solid support-polymethylaluminoxane complex. The measurement apparatus employed was BELSORP mini II made by BEL Japan, Inc., and the measurement gas was nitrogen gas.

Conversion Equation for BET Measurement Values:

Specific surface area ($m^2$/mmol-Al) per quantity of Al contained in the solid support-polymethylaluminoxane complex=BET measurement value ($m^2/g$)*27/10Y (wt %)

(3) Volume-Based Median Diameter and Particle Size Distribution of Solid Support-Polymethylaluminoxane Complex The volume-based median diameter and particle size distribution of solid support-polymethylaluminoxane complex were determined by the laser diffraction and scattering method under a dry nitrogen atmosphere with a Master Sizer 2000 Hydro S made by Malvern Instrument Ltd. Primarily dehydrated and degassed n-hexane was employed as the dispersion medium, with dehydrated and degassed toluene being employed on some occasions depending on the objective. Homogeneity as defined by the following equation was employed as an indicator of catalyst particle size distribution:

$$\text{Homogeneity} = \Sigma Xi|d(0.5)-Di|/d(0.5)\Sigma Xi$$

Here, Xi denotes the histogram value of a particle i, d(0.5) denotes the volume-based median diameter, and Di denotes the volume-based diameter of a particle i.

(4) Mole Fraction of Methyl Groups

The mole fractions of the various components in the polymethylaluminoxane composition were determined from the surface area ratios assigned to the various components in $^1$H-NMR measurement of the polymethylaluminoxane composition. An example of the methods of determining the specific Me(PMAO) and Me (TMAL) mole fractions of the polymethylaluminoxane composition are given below. The mole fraction of methyl groups contributed from polymethylaluminoxane is denoted as Me(PMAO). The mole fraction of methyl groups contributed from trimethylaluminium is denoted by Me (TMAL).

Figure 1:
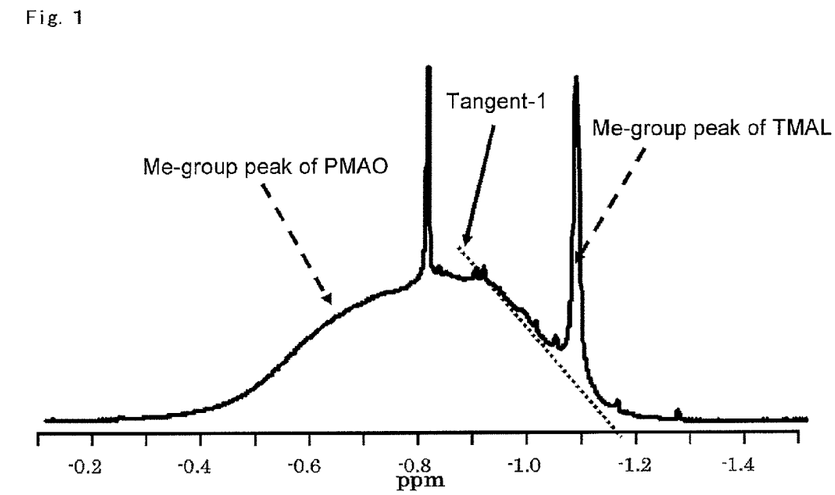
FIG. 1 A ¹H-NMR chart of a solution polymethylaluminoxane composition obtained according to the present invention.

First, $^1$H-NMR measurement of the polymethylaluminoxane composition was conducted with $d_8$-THF as a deuterated solvent. The $^1$H-NMR measurement was conducted at a measurement temperature of 24° C. with a Gemini 2000 300 MHz NMR measurement apparatus from Varian Technologies Japan, Ltd. An example of a $^1$H-NMR chart is given in FIG. 1.
(i) The full integral value of the peak of Me groups of polymethylaluminoxane including trimethylaluminoxane, which appeared at from about −0.3 ppm to −1.2 ppm, was determined and adopted as I (polymethylaluminoxane).
(ii) The peak of Me groups contributed from TMAL in the vicinity of −1.1 ppm was cut by tangent-1, and the integral value I (TMAL-Me) was determined.
(iii) The integral value determined in (ii) was subtracted from integral value I (polymethylaluminoxane) determined in (i) to determine the Me-group integral value I (PMAO-Me) of just the polymethylaluminoxane without the trimethylaluminum. I (TMAL-Me) and I (PMAO-Me) were normalized by division by I (polymethylaluminoxane) to determine the mole fractions of Me(PMAO) and Me (TMAL).

The various peaks can be conveniently cut out by methods employing commercially available curve fitting programs and by methods employing baseline collection.

Further, the analysis sample of the solution polymethylaluminoxane composition was prepared by adding about 0.5 mL of $d_8$-THF to about 0.05 mL of solution polymethylaluminoxane composition. The analysis sample of solid support-polymethylaluminoxane complex was prepared by adding 0.5 mL of $d_8$-THF to 10 mg of solid support polymethylaluminoxane complex.

The following reactions were conducted in a dry nitrogen gas atmosphere. All solvents employed had been dehydrated and degassed.

Preliminary Test 1

Benzoic Acid-Al/O=1.40

(1) Synthesis of Solution Polymethylaluminoxane Composition

To a separable flask with an internal volume of 2 L equipped with a stirring apparatus were charged 240.8 g (3.34 mol) of trimethylaluminum (TMAL) and 600.5 g of toluene. The solution was cooled to 15° C. and 145.7 g (1.19 mol) of benzoic acid was gradually added at a rate such that the temperature of the solution remained at 25° C. or lower. Subsequently, heating and aging were conducted for 1 hour at 50° C. At that time, the molar ratio of TMAL to oxygen atoms in the benzoic acid was 1.40. The reaction solution was heated for 4 hours at 70° C. and then heated to 60° C. for 6 hours to obtain a toluene solution of polymethylaluminoxane composition. The solution obtained was a transparent, gel-free liquid. The results of aluminum analysis conducted after recovery of the reaction solution revealed a quantitative reaction yield based on aluminum atoms. The concentration of aluminum in the reaction solution obtained was 9.30 wt %. The quantity of Me (TMAL) in the solution polymethylaluminoxane composition obtained as determined by $^1$H-NMR was 26.0 mol %. Since the solution polymethylaluminoxane composition was in the form of a solution, the measurement of solubility that is specified in the test method section was precluded. However, the concentration in toluene as determined by calculating the specific gravity and aluminum concentration of the solution was about 3.1 mol/L.

When polymethylaluminoxane that had been concentrated and dried was dissolved in benzene, the molecular weight as determined by the freezing point depression method was 2,430. Accordingly, the degree of polymerization n of the aluminoxane was determined to be 42.

(2) Ethylene Polymerization Evaluation

To a 500 mL, four-necked flask equipped with magnetic stirring apparatus was charged 250 mL of toluene and the flask was heated to 34° C. To this was added, based on aluminum atoms, 0.16 g (5.93 mmol) of polymethylaluminoxane toluene solution, to which bis(cyclopentadienyl)zirconium dichloride ($Cp_2ZrCl_2$) was added to achieve an Al/Zr molar ratio of 5,000. While heating the mixture to 40° C., ethylene gas was blown in. Ten minutes later, the supply of ethylene gas was halted and methanol was introduced to deactivate the catalyst. The polyethylene produced was filtered out and dried. The polymerization activity was determined to be $62 \times 10^6$ g-PE/mol-Zr·atm·hr. The polymer was amorphous in shape, and there was pronounced fouling of the polymerization apparatus.

Preliminary Test 2

Benzoic Acid-Al/O=1.20

(1) Synthesis of Solution Polymethylaluminoxane Composition

With the exception that the quantity of benzoic acid introduced to the powder in Preliminary Test 1 was changed so that the molar ratio of TMAL to oxygen atoms in the benzoic acid was 1.20 and the heating following the heating and aging at 50° C. was conducted for 32 hours at 70° C., a solution polymethylaluminoxane composition was synthesized in the same manner as in Preliminary Test 1. The solution obtained was a transparent, gel-free liquid. The results of aluminum analysis conducted after recovery of the reaction solution revealed a quantitative reaction yield based on aluminum atoms. The concentration of aluminum in the reaction solution obtained was 9.04 wt %. The quantity of Me (TMAL) in the solution polymethylaluminoxane composition obtained as determined by $^1$H-NMR was 14.0 mol %. Since the solution polymethylaluminoxane composition was in the form of a solution, the measurement of solubility that is specified in the test method section was precluded. However, the concentration in toluene as determined by calculating the specific gravity and aluminum concentration of the solution was about 3.0 mol/L.

(2) Ethylene Polymerization Evaluation

Polymerization evaluation conducted by the same method as that described in (2)1. of Preliminary Test 1 revealed the polymerization activity to be $39 \times 10^6$ g-PE/mol-Z·atm·hr. The polymer was amorphous in shape. The molecular weight as determined by high temperature GPC was 180,000. Mw/Mn was 2.9. The polymer was amorphous in shape, and there was pronounced fouling of the polymerization apparatus.

Example 1

(1) Synthesis of Solid Support-Polymethylaluminoxane Complex

To a round-bottomed flask with an internal volume of 300 mL equipped with stirring apparatus were charged 29.55 g (98.9 mol-Al) of a toluene solution of the polymethylaluminoxane composition prepared in Preliminary Test 2 (Al/O=1.20) and 10.0 g of $SiO_2$ (P-10 $SiO_2$ made by Fuji Silysia, average particle diameter 41.0 μm, specific surface area 276 $m^2/g$) that had been sintered at 750° C. for 4 hours in $N_2$. The mixture was heated for 8 hours at 100° C. with stirring. The solution was then cooled to 30° C. or lower, after which the supernatant was removed by decantation. The slurry obtained was washed twice in 200 mL of n-hexane to clean it. The solid obtained was dried under reduced pressure at room temperature to obtain a dry, solid polymethylaluminoxane composition. The precipitation rate of the dry, solid polymethylaluminoxane composition was 99.7% based on the aluminum atoms in the solution polymethylaluminoxane composition employed, making it nearly quantitative. No elimination of solid matter was visually observed during synthesis.

(2) Synthesis of Solid Support-Polymethylaluminoxane Complex (a) The Aluminum Content The aluminum content of the dried, solid support-polymethylaluminoxane complex was measured at 16.10 wt %—Al. Based on these results, the aluminum content of the coating layer containing polymethylaluminoxane and trimethylaluminum was determined to be 40.8 wt %—Al. An overview of the calculation method is given below.

(Method of Determining Al Content of Coating Layer)

(i) Of the aluminum component contained in the toluene solution of the polymethylaluminoxane composition employed, 99.7% formed a complex with $SiO_2$. Accordingly, 2.66 g—Al (=98.9 mmol×99.7/100×26.98 g/mol×1/1000) adhered to the surface of the support.

(ii) Since no solid matter was removed in synthesis, all 10 g of the $SiO_2$ employed was recovered as catalyst.

(iii) Since the aluminum content of the complex obtained was 16.1 wt %—Al, the weight adhering to the complex was 6.521 g (=(2.66/16.1×100)−10).

(iv) Using the results of the above calculations, the aluminum content of the coating layer was determined to be 40.8 wt %—Al (=2.66/6.521×100).

(b) Shape Evaluation

Evaluation of the particle size distribution of the dried, solid support-polymethylaluminoxane complex by Master Sizer 2000 Hydro S revealed a volume-based median diameter d(0.5) of 44.8 μm. The homogeneity was 0.92.

Figure 2:
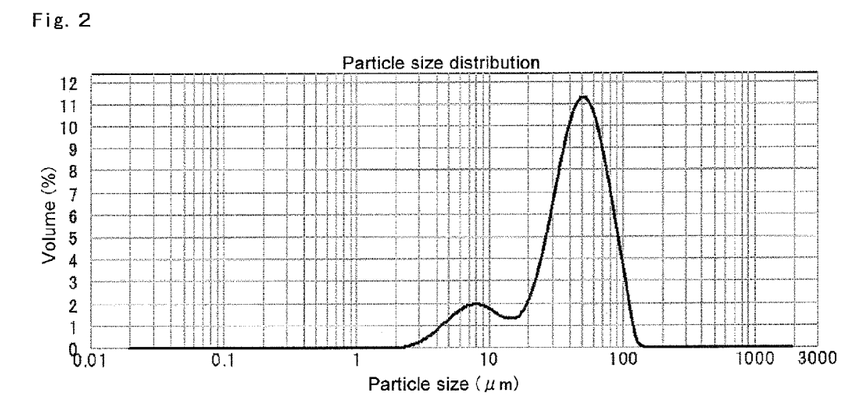
FIG. 2 The results of particle size distribution evaluation with a Master Sizer 2000 Hydro S of the dried solid support-polymethylaluminoxane complex of Example 1.
Figure 8:
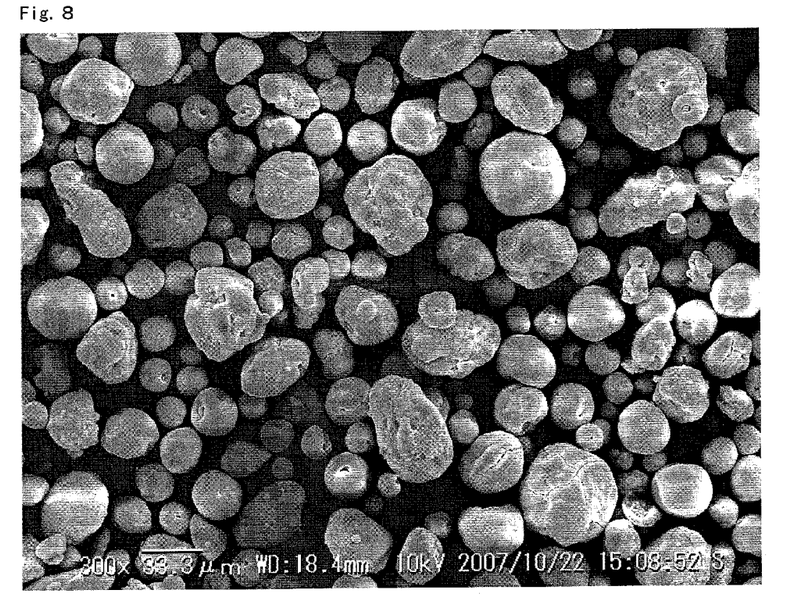
FIG. 8 A SEM photograph (300-fold magnification) of the $SiO_2$ (P-10, $SiO_2$ made by Fuji Silysia) employed in the Examples prior to formation of the coating layer of polymethylaluminoxane composition.

FIG. 2 shows the particle size distribution chart obtained. The peak of about 10 μm is due to minute particles contained in the $SiO_2$ employed. The coating layer was also formed of these minute particles. For reference, a SEM photograph (300-fold magnification) of the $SiO_2$ (P-10, $SiO_2$ made by Fuji Silysia) prior to formation of the coating layer on the polymethylaluminoxane composition is given in FIG. 8.

(c) Measurement of the Specific Surface Area

Measurement of the specific surface area of the dried, solid support-polymethylaluminoxane complex revealed the specific surface area per mmol of aluminum atoms to be 55.3 $m^2$/mmol-Al.

(d) SEM Photography

Figure 3:
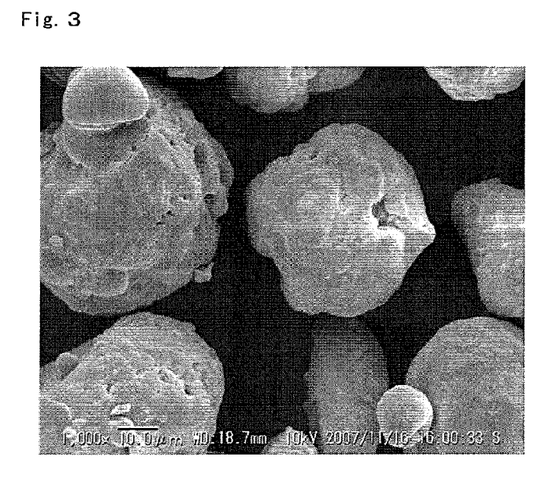
FIG. 3 An SEM photograph (1,000-fold magnification) of the dried solid support-polymethylaluminoxane complex of Example 1.

SEM photography of the dried, solid support-polymethylaluminoxane complex yielded the following SEM photograph (FIG. 3, 1,000-fold magnification).

(e) Me (TMAL) Quantity $^1$H-NMR measurement revealed the Me (TMAL) quantity to be 9.0 mol %.

(3) Ethylene Polymerization Evaluation

To a 500 mL four-necked flask equipped with magnetic stirring apparatus was charged 250 mL of toluene and the contents of the flask were heated to 34° C. To this was added a toluene slurry solution of 0.16 g (5.93 mmol) of solid support-polymethylaluminoxane complex based on aluminum atoms, to which bis(cyclopentadienyl)zirconium dichloride ($Cp_2ZrCl_2$) was added to achieve an Al/Zr molar ratio of 5,000. While heating the mixture to 40° C., ethylene gas was blown in. Ten minutes later, the supply of ethylene gas was halted and methanol was introduced to deactivate the catalyst. The polyethylene produced was filtered out and dried. The polymerization activity was determined to be $30.2 \times 10^6$ g-PE/mol-Zr·atm·hr.

The polymer obtained had a free-flowing microparticulate shape, and did not adhere to the reactor following polymerization. The molecular weight as measured by high-temperature GPC was 180,000. The Mw/Mn was 2.7.

Example 2

(1) Synthesis of Solid Support-Polymethylaluminoxane Complex

With the exception that a toluene solution of the polymethylaluminoxane composition prepared in Preliminary Test 1 (Al/O=1.40) was employed in a 300 mL round-bottomed flask equipped with stirring apparatus, a dry, solid polymethylaluminoxane composition was obtained in the same manner as in Example 1(1). The precipitation rate of the dry, solid polymethylaluminoxane composition, at 95.1% based on the aluminum atoms of the solution polymethylaluminoxane composition employed, was lower than in Example 1(1). No loss of solid matter was visually observed during synthesis.

(2) Analysis of Solid Support-Polymethylaluminoxane Complex (a) Aluminum Content The aluminum content of the dried, solid support-polymethylaluminoxane complex was measured at 15.5 wt %—Al. Based on these results, the aluminum content, of the coating layer containing polymethylaluminoxane and trimethylaluminum was determined to be 39.8 wt %—Al.

(b) Shape Evaluation

Evaluation of the particle size distribution of the dried, solid support-polymethylaluminoxane complex by Master Sizer 2000 Hydro S revealed a volume-based median diameter d(0.5) of 43.0 μm. The homogeneity was 0.95.

(c) Measurement of the Specific Surface Area

Measurement of the specific surface area of the dried, solid support-polymethylaluminoxane complex revealed the specific surface area per mmol of aluminum atoms to be 61.2 $m^2$/mmol-Al.

(d) Me (TMAL) Quantity $^1$H-NMR measurement revealed the Me (TMAL) quantity to be 11.4 mol %.

(3) Ethylene Polymerization Evaluation

To a 500 mL four-necked flask equipped with magnetic stirring apparatus was charged 250 mL of toluene and the contents of the flask were heated to 34° C. To this was added a toluene slurry solution of 0.16 g (5.93 mmol) of solid support-polymethylaluminoxane complex based on aluminum atoms, to which bis(cyclopentadienyl)zirconium dichloride ($Cp_2ZrCl_2$) was added to achieve an Al/Zr molar ratio of 5,000. While heating the mixture to 40° C., ethylene gas was blown in. Ten minutes later, the supply of ethylene gas was halted and methanol was introduced to deactivate the catalyst. The polyethylene produced was filtered out and dried. The polymerization activity was determined to be $27.3 \times 10^6$ g-PE/mol-Zr·atm·hr.

The polymer obtained had a free-flowing microparticulate shape, and did not adhere to the reactor following polymerization. The molecular weight as measured by high-temperature GPC was 170,000. The Mw/Mn was 2.8.

Example 3

(1) Synthesis of Solid
Support-Polymethylaluminoxane Complex (a) Preparation of TMAL Processed $SiO_2$ To a 1 L flask equipped with magnetic stirring apparatus were charged 29.37 g of $SiO_2$ (P-10, $SiO_2$ made by Fuji Silysia) that had been sintered for 2 hours at 400° C. and 510 mL of hexane. With stirring, 43.72 g (TMAL 57.0 mmol) of a hexane solution of TMAL was added at room temperature and the mixture was heated and aged at 50° C. After cooling to room temperature, the supernatant was removed by decantation. The mixture was washed three times with 500 mL of hexane and dried under reduced pressure at room temperature, yielding 30.8 g of dry TMAL processed $SiO_2$. The Al concentration of the solid obtained was 4.6 wt %—Al.

(b) Synthesis of Solid Support-Polymethylaluminoxane Complex

With the exception that TMAL processed $SiO_2$ was employed instead of $SiO_2$, a dried, solid polymethylaluminoxane composition was obtained by the same method as that described in Example 1(1) using the toluene solution of polymethylaluminoxane composition prepared in Preliminary Test 2 (Al/O=1.20). The precipitation rate of the dry, solid polymethylaluminoxane composition was 95.4% based on the aluminum atoms in the solution polymethylaluminoxane composition employed, making it nearly quantitative. No elimination of solid matter was visually observed during synthesis.

(2) Analysis of Solid
Support-Polymethylaluminoxane Complex (a) Aluminum Content The aluminum content of the dried, solid support-polymethylaluminoxane complex was measured at 17.3 wt %—Al. Based on these results, the aluminum content of the coating layer containing polymethylaluminoxane and trimethylaluminum was determined to be 36.9 wt %—Al.

(b) Shape Evaluation

Evaluation of the particle size distribution of the dried, solid support-polymethylaluminoxane complex by Master Sizer 2000 Hydro S revealed a volume-based median diameter d(0.5) of 47.0 μm. The homogeneity was 0.89.

(c) Measurement of the Specific Surface Area

Measurement of the specific surface area of the dried, solid support-polymethylaluminoxane complex revealed the specific surface area per mmol of aluminum atoms to be 55.3 $m^2$/mmol-Al.

(d) Me (TMAL) Quantity $^1$H-NMR measurement revealed the Me (TMAL) quantity to be 8.5 mol %.

(3) Ethylene Polymerization Evaluation

To a 500 mL four-necked flask equipped with magnetic stirring apparatus was charged 250 mL of toluene and the contents of the flask were heated to 34° C. To this was added a toluene slurry solution of 0.16 g (5.93 mmol) of solid support-polymethylaluminoxane complex based on aluminum atoms, to which bis(cyclopentadienyl)zirconium dichloride ($Cp_2ZrCl_2$) was added to achieve an Al/Zr molar ratio of 5,000. While heating the mixture to 40° C., ethylene gas was blown in. Ten minutes later, the supply of ethylene gas was halted and methanol was introduced to deactivate the catalyst. The polyethylene produced was filtered out and dried. The polymerization activity was determined to be $23.0 \times 10^6$ g-PE/mol-Z·atm·hr.

The polymer obtained had a free-flowing microparticulate shape, and did not adhere to the reactor following polymerization. The molecular weight as measured by high-temperature GPC was 160,000. The Mw/Mn was 2.6.

Example 4

(1) Synthesis of Solid
Support-Polymethylaluminoxane Complex

With the exception that 50 mg of carbon nanotube (Aldrich, Multi-walled, synthesized by CVD, OD 20 to 30 nm, wall thickness 1 to 2 nm, length 0.5 to 2 μm) was employed instead of $SiO_2$ as the solid support, a dry, solid polymethylaluminoxane composition was obtained in the same manner as in Example 1(1). The precipitation rate of the dry, solid polymethylaluminoxane composition, at 99.0% based on the aluminum atoms of the solution polymethylaluminoxane composition employed, was nearly quantitative. No loss of solid matter was visually observed during synthesis.

(2) Analysis of Solid
Support-Polymethylaluminoxane Complex (a) Aluminum Content The aluminum content of the dried, solid support-polymethylaluminoxane complex was measured at 36.3 wt %—Al. Based on these results, the aluminum content of the coating layer containing polymethylaluminoxane and trimethylaluminum was determined to be 36.5 wt %—Al.

(b) Shape Evaluation

Figure 4:
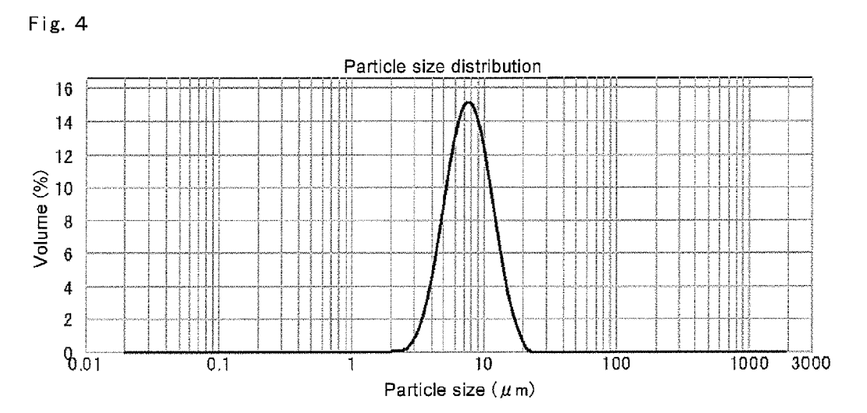
FIG. 4 Particle size distribution evaluation with a Master Sizer 2000 Hydro S of the dried solid support-polymethylaluminoxane complex of Example 4.

Evaluation of the particle size distribution of the dried, solid support-polymethylaluminoxane complex by Master Sizer 2000 Hydro S revealed a volume-based median diameter d(0.5) of 7.8 μm. The homogeneity was 0.32. A particle size distribution chart is shown in FIG. 4.

(c) Measurement of the Specific Surface Area

Measurement of the specific surface area of the dried, solid support-polymethylaluminoxane complex revealed the specific surface area per mmol of aluminum atoms to be 31.2 $m^2$/mmol-Al.

(d) SEM Photography

Figure 5:
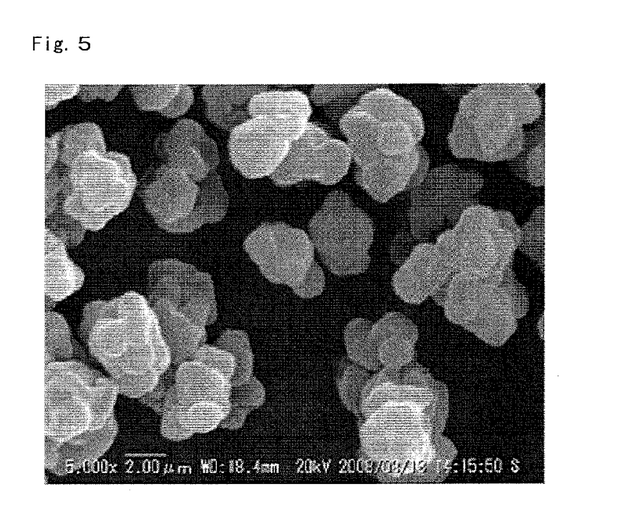
FIG. 5 An SEM photograph (5,000-fold magnification) of the dried solid support-polymethylaluminoxane complex of Example 4.

SEM photography of the dried, solid support-polymethylaluminoxane complex yielded the following SEM photograph (FIG. 5, 5,000-fold magnification).

(e) Me (TMAL) Quantity $^1$H-NMR measurement revealed the Me (TMAL) quantity to be 8.8 mol %.

(3) Ethylene Polymerization Evaluation

Ethylene polymerization evaluation was conducted on the solid support-polymethylaluminoxane complex by the same polymerization method as that described in Example 1(3). The polyethylene produced was filtered out and dried. The polymerization activity was determined to be $60.3 \times 10^6$ g-PE/mol-Zr·atm·hr.

The polymer obtained had a free-flowing microparticulate shape, and did not adhere to the reactor following polymerization. The molecular weight as measured by high-temperature GPC was 200,000. The Mw/Mn was 2.5.

Example 5

(1) Synthesis of Solid Support-Polymethylaluminoxane Complex

With the exception that 150 mg of carbon nanotube (Aldrich, Multi-walled, synthesized by CVD, OD 20 to 30 nm, wall thickness 1 to 2 nm, length 0.5 to 2 μm) was employed instead of $SiO_2$ as the solid support, a dry, solid polymethylaluminoxane composition was obtained in the same manner as in Example 1(1). The precipitation rate of the dry, solid polymethylaluminoxane composition (coating layer), at 99.2% based on the aluminum atoms of the solution polymethylaluminoxane composition employed, was nearly quantitative. No loss of solid matter was visually observed during synthesis.

(2) Analysis of Solid Support-Polymethylaluminoxane Complex (a) Aluminum Content The aluminum content of the dried, solid support-polymethylaluminoxane complex was measured at 38.3 wt %—Al. Based on these results, the aluminum content of the coating layer containing polymethylaluminoxane and trimethylaluminum was determined to be 39.2 wt %—Al.

(b) Shape Evaluation

Figure 6:
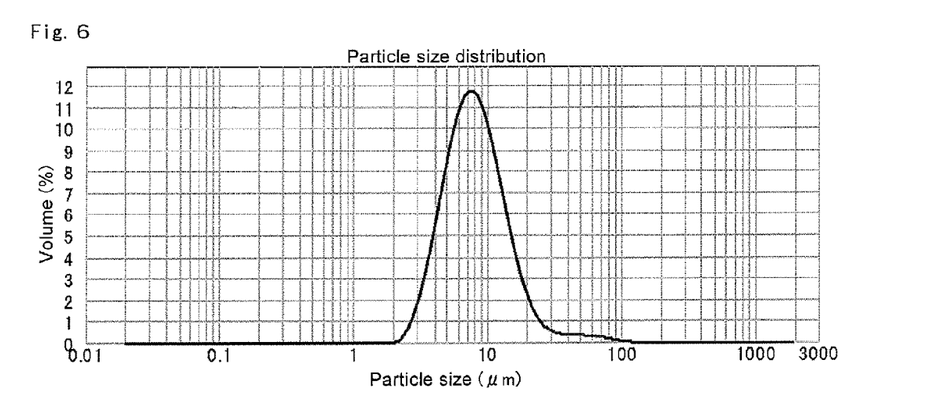
FIG. 6 Particle size distribution evaluation with a Master Sizer 2000 Hydro S of the dried solid support-polymethylaluminoxane complex of Example 5.

Evaluation of the particle size distribution of the dried, solid support-polymethylaluminoxane complex by Master Sizer 2000 Hydro S revealed a volume-based median diameter d(0.5) of 8.0 μm. The homogeneity was 0.55. A particle size distribution chart is shown in FIG. 6.

(c) Measurement of the Specific Surface Area

Measurement of the specific surface area of the dried, solid support-polymethylaluminoxane complex revealed the specific surface area per mmol of aluminum atoms to be 35.1 $m^2$/mmol-Al.

(d) SEM Photography

Figure 7:
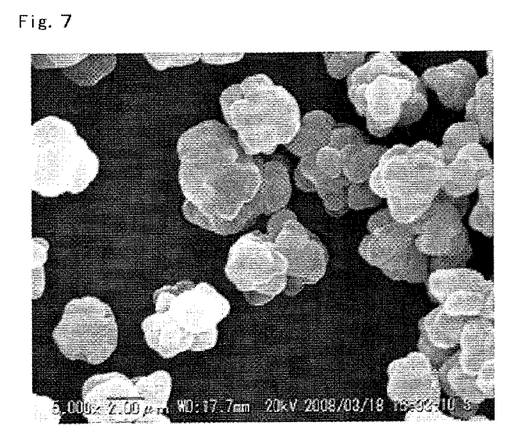
FIG. 7 A SEM photograph (5,000-fold magnification) of the dried solid support-polymethylaluminoxane complex of Example 5.

SEM photography of the dried, solid support-polymethylaluminoxane complex yielded the following SEM photograph (FIG. 7, 5,000-fold magnification).

(e) Me (TMAL) Quantity $^1$H-NMR measurement revealed the Me (TMAL) quantity to be 8.0 mol %.

(3) Ethylene Polymerization Evaluation

Ethylene polymerization evaluation was conducted on the solid support-polymethylaluminoxane complex by the same polymerization method as that described in Example 1(3). The polyethylene produced was filtered out and dried. The polymerization activity was determined to be $65.3 \times 10^6$ g-PE/mol-Z·atm·hr.

The polymer obtained had a free-flowing microparticulate shape, and did not adhere to the reactor following polymerization. The molecular weight as measured by high-temperature GPC was 190,000. The Mw/Mn was 2.6.

Reference Example 1

The results of ethylene synthesis described in Example 1 of Japanese Unexamined Patent Publication (KOKAI) Showa No. 61-108610 (Patent Reference 3) were converted to a polymerization activation value per hour of the polymerization period for an ethylene pressure of 1 atmosphere and 1 mol of zirconium, yielding $8.9 \times 10^5$ g-PE/mol-Z·atm·hr. This polymerization activity was lower by a decimal place than that achieved using the solid support-polymethylaluminoxane complex of the present invention described in the above-mentioned Examples.

Example 6

(1) Synthesis of Solid Support-Polymethylaluminoxane Complex

With the exception that 1 g of carbon nanotube (Aldrich, Multi-walled, synthesized by CVD, OD 20 to 30 nm, wall thickness 1 to 2 nm, length 0.5 to 2 μm) was employed instead of $SiO_2$ as the solid support, a dry, solid polymethylaluminoxane composition was obtained in the same manner as in Example 1(1). The precipitation rate of the dry, solid polymethylaluminoxane composition (coating layer), at 99.5% based on the aluminum atoms of the solution polymethylaluminoxane composition employed, was nearly quantitative. No loss of solid matter was visually observed during synthesis.

(2) Analysis of Solid Support-Polymethylaluminoxane Complex (a) Aluminum Content The aluminum content of the dried, solid support-polymethylaluminoxane complex was measured at 33.3 wt %—Al. Based on these results, the aluminum content of the coating layer containing polymethylaluminoxane and trimethylaluminum was determined to be 38.1 wt %—Al.

(b) Shape Evaluation

Evaluation of the particle size distribution of the dried, solid support-polymethylaluminoxane complex by Master Sizer 2000 Hydro S revealed a volume-based median diameter d(0.5) of 11.0 μm. The homogeneity was 0.55.

(c) Measurement of the Specific Surface Area

Measurement of the specific surface area of the dried, solid support-polymethylaluminoxane complex revealed the specific surface area per mmol of aluminum atoms to be 40.1 $m^2$/mmol-Al.

(d) Me (TMAL) Quantity $^1$H-NMR measurement revealed the Me (TMAL) quantity to be 9.0 mol %.

(3) Ethylene Polymerization Evaluation

Ethylene polymerization evaluation was conducted on the solid support-polymethylaluminoxane complex by the same polymerization method as that described in Example 1(3). The polyethylene produced was filtered out and dried. The polymerization activity was determined to be $70.3 \times 10^6$ g-PE/mol-Zr·atm·hr.

The polymer obtained had a free-flowing microparticulate shape, and did not adhere to the reactor following polymerization.

Example 7

(1) Synthesis of Solid Support-Polymethylaluminoxane Complex

With the exception that 5 g of carbon nanotube (Aldrich, Multi-walled, synthesized by CVD, OD 20 to 30 nm, wall thickness 1 to 2 nm, length 0.5 to 2 μm) was employed instead of $SiO_2$ as the solid support, a dry, solid polymethylaluminoxane composition was obtained in the same manner as in Example 1(1). The precipitation rate of the dry, solid polymethylaluminoxane composition (coating layer), at 99.2% based on the aluminum atoms of the solution polymethylaluminoxane composition employed, was nearly quantitative. No loss of solid matter was visually observed during synthesis.

(2) Analysis of Solid Support-Polymethylaluminoxane Complex (a) Aluminum Content
The aluminum content of the dried, solid support-polymethylaluminoxane complex was measured at 22.9 wt %—Al. Based on these results, the aluminum content of the coating layer containing polymethylaluminoxane and trimethylaluminum was determined to be 40.3 wt %—Al.
(b) Shape Evaluation
Evaluation of the particle size distribution of the dried, solid support-polymethylaluminoxane complex by Master Sizer 2000 Hydro S revealed a volume-based median diameter d(0.5) of 25.0 μm. The homogeneity was 0.62.
(c) Measurement of the Specific Surface Area
Measurement of the specific surface area of the dried, solid support-polymethylaluminoxane complex revealed the specific surface area per mmol of aluminum atoms to be 60.1 $m^2$/mmol-Al.
(d) Me (TMAL) Quantity
$^1$H-NMR measurement revealed the Me (TMAL) quantity to be 8.2 mol %.

(3) Ethylene Polymerization Evaluation

Ethylene polymerization evaluation was conducted on the solid support-polymethylaluminoxane complex by the same polymerization method as that described in Example 1(3). The polyethylene produced was filtered out and dried. The polymerization activity was determined to be 70.3×10⁶ g-PE/mol-Zr·atm·hr.

The polymer obtained had a free-flowing microparticulate shape, and did not adhere to the reactor following polymerization.

Example 8

(1) Synthesis of Solid Support-Polymethylaluminoxane Complex

With the exception that 10.0 g of carbon nanotube (Aldrich, Multi-walled, synthesized by CVD, OD 20 to 30 nm, wall thickness 1 to 2 nm, length 0.5 to 2 μm) was employed instead of $SiO_2$ as the solid support, a dry, solid polymethylaluminoxane composition was obtained in the same manner as in Example 1(1). The precipitation rate of the dry, solid polymethylaluminoxane composition (coating layer), at 99.0% based on the aluminum atoms of the solution polymethylaluminoxane composition employed, was nearly quantitative. No loss of solid matter was visually observed during synthesis.

(2) Analysis of Solid Support-Polymethylaluminoxane Complex (a) Aluminum Content
The aluminum content of the dried, solid support-polymethylaluminoxane complex was measured at 15.8 wt %—Al. Based on these results, the aluminum content of the coating layer containing polymethylaluminoxane and trimethylaluminum was determined to be 39.3 wt %—Al.
(b) Shape Evaluation
Evaluation of the particle size distribution of the dried, solid support-polymethylaluminoxane complex by Master Sizer 2000 Hydro S revealed a volume-based median diameter d(0.5) of 45.0 μm. The homogeneity was 0.75.
(c) Measurement of the Specific Surface Area
Measurement of the specific surface area of the dried, solid support-polymethylaluminoxane complex revealed the specific surface area per mmol of aluminum atoms to be 93.5 $m^2$/mmol-Al.
(d) Me (TMAL) Quantity
$^1$H-NMR measurement revealed the Me (TMAL) quantity to be 7.8 mol %.

(3) Ethylene Polymerization Evaluation

Ethylene polymerization evaluation was conducted on the solid support-polymethylaluminoxane complex by the same polymerization method as that described in Example 1(3). The polyethylene produced was filtered out and dried. The polymerization activity was determined to be 75.3×10⁶ g-PE/mol-Z·atm·hr.

The polymer obtained had a free-flowing microparticulate shape, and did not adhere to the reactor following polymerization.

INDUSTRIAL APPLICABILITY

The present invention is useful in the technical field of producing polyolefins.

The invention claimed is:
1. A supported polymethylaluminoxane composition solid particle comprising a coated layer of polymethylaluminoxane composition, wherein:
the supported polymethylaluminoxane composition includes trimethylaluminum and polymethylaluminoxane represented by formula (I):

—[(Me)AlO]$_n$—, an aluminum content of the polymethylaluminoxane composition is 36 to 41 mass %,
a mole fraction of methyl groups contributed from trimethylaluminum moieties relative to total moles of methyl groups is about 12 mol % or less, and
wherein the supported polymethylaluminoxane composition solid particle is prepared by heating an unsupported polymethylaluminoxane composition in an aromatic hydrocarbon solution together with a solid support at a temperature in the range of about 80 to 200° C. for a period of about 5 minutes to less than 24 hours.

2. The particle according to claim 1, wherein the particle is prepared by heating at a temperature in the range of about 90 to 150° C.

3. The particle according to claim 1, wherein the particle is prepared by heating for a period of about 5 hours to less than 24 hours.

4. The particle according to claim 1, wherein the supported polymethylaluminoxane is represented by formula (I-A):

$$—[(Me)AlO]_n— \tag{I-A}$$

n is an integer from about 10 to 50.

5. The particle according to claim 1, wherein the unsupported polymethylaluminoxane is represented by formula (I-A):

$$—[(Me)AlO]_n— \tag{I-B}$$

n is an integer from about 1 to 50.

6. An olefin polymerization catalyst comprising the solid support-polymethylaluminoxane complex according to claim 1 and a transition metal compound represented by formula (III):

$$MR^5R^6R^7R^8 \tag{III}$$

$R^5$, $R^6$, $R^7$, and $R^8$ are organic groups having a cycloalkadienyl skeleton joined with an alkyl group, alkoxy group, aryloxy group, alkylsilyl group, alkylamide group, alkylimide group, alkylamine group, alkylimine group, or halogen atom, and M is a transition metal.

7. A method for producing a polyolefin, comprising polymerizing an olefin using the catalyst according to claim 6.

* * * * *